United States Patent [19]

Teipel

[11] 4,039,285

[45] Aug. 2, 1977

[54] SINGLE SAMPLE METHOD FOR DETERMINATION OF LIPOPROTEIN CONCENTRATIONS IN BLOOD

[75] Inventor: John William Teipel, Belle Meade, N.J.

[73] Assignee: Ortho Diagnostics, Inc., Raritan, N.J.

[21] Appl. No.: 621,339

[22] Filed: Oct. 10, 1975

[51] Int. Cl.² ............................................ G01N 33/16
[52] U.S. Cl. .................................... 23/230 B; 252/408
[58] Field of Search ........................ 23/230 B; 252/408

[56] References Cited

U.S. PATENT DOCUMENTS

| | | | |
|---|---|---|---|
| 3,436,187 | 4/1969 | Ferro et al. | 23/230 B |
| 3,479,154 | 11/1969 | Cardinal | 23/230 B |
| 3,558,516 | 1/1971 | Wybenga | 23/230 B X |
| 3,791,791 | 2/1974 | Finkel et al. | 23/230 B |

OTHER PUBLICATIONS

Scholnick et al. "Protides of the Biological Fluids, Proceedings of the 19th Coloquiuum 1971", H. Peeters, Ed. pp. 289-292.
Searcy et al. "A Screening Procedure for Detecting and Characterizing Hyperlipoproteinemia", Clinica Chimica Acta, 38 (1972) 291–300.
Stone et al. "A New Technique for the Investigation of the Low-Density Lipoproteins in Health and Disease", Clinica Chimica Acta, 14 (1966) 812–830.
Stone et al. "Diagnosis and Classification of Abnormal Lipoprotein Patterns", Clinica Chimica Acta, 31 (1971) 333–354.

*Primary Examiner*—Joseph Scovronek
*Assistant Examiner*—Arnold Turk

[57] ABSTRACT

A single-sample method for determining concentrations of individual lipoprotein classes and lipids in blood by turbidimetric measurement. The blood serum is mixed with an ionic-strength-sensitive agent for forming an insoluble complex with the chylomicron, very low density, and low density lipoprotein classes, and the ionic strength of the mixture is raised in steps to cause progressive dissolution of each class of complex from that of highest density lipoprotein to that of lowest density lipoprotein. Measurement of the turbidity due to the insoluble complex(es) present at each step allows calculation of the turbidity due to the complex of each individual lipoprotein class and from that the concentration of each lipoprotein class and lipid in the blood sample.

20 Claims, 3 Drawing Figures

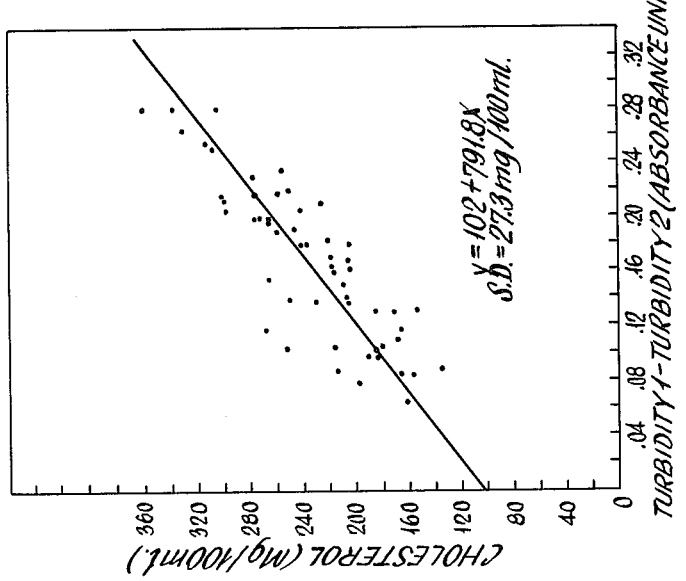
Fig. 1. Relationship between turbidity 1 and sum of cholestrol plus triglyceride.
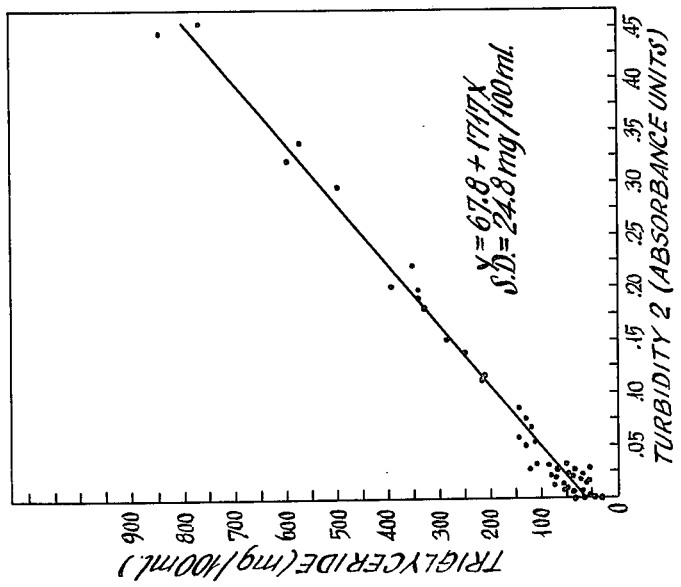
Fig. 2. Relationship between turbidity 2 and triglyceride.
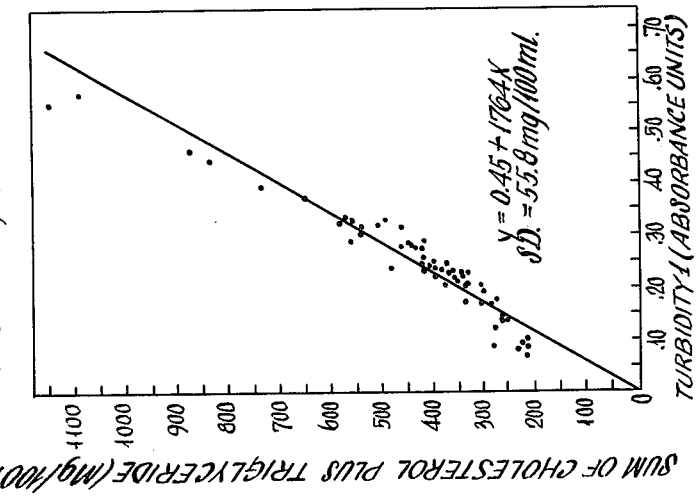
Fig. 3. Relationship between turbidity 1 minus turbidity 2 and cholestrol.

SINGLE SAMPLE METHOD FOR DETERMINATION OF LIPOPROTEIN CONCENTRATIONS IN BLOOD

BACKGROUND OF THE INVENTION

The present invention relates to methods for determining concentrations of lipoproteins and lipids in blood and, more particularly, to such methods which utilize turbidimetric measurement.

Lipoproteins are aggregates of lipids and protein which circulate in the blood and are the means by which lipids are transported within the body. The lipid portions of these aggregates consist essentially of chloessterol and triglyceride. The various classes of lipoproteins contain cholesterol and triglyceride in different proportions and from different proportions and from different sources. Thus, by determining the concentrations of the various lipoprotein classes in blood, one can determine the concentrations of cholesterol and triglyceride. Since the concentrations of both lipoproteins and lipis correlate with the incidence of various circulatory and coronary diseases, they are of great medical importance. Lipoproteins are divided into four major classes based on their behavior in prior art methods of analysis. These classes are: chylomicrons (abbreviated herein as CHYLO), very low density lipoproteins (also known as pre-beta lipoproteins and abbreviated herein as VLDL), low density lipoproteins (also known as beta lipoproteins and abbreviated herein as LDL) and high density lipoproteins (also known as alpha lipoproteins and abbreviated herein as HDL). Minor classes such as, for example, floating beta lipoproteins, lipoprotein X, sinking pre-beta lipoproteins, and the like occur less frequently. The presence of an abnormally high level of certain of these classes of lipoproteins has been correlated with various disorders, conveniently expressed according to the system of Frederickson, et al. In this classification system, the presence of various clinical disorders is related to elevated levels of various classes of lipoproteins. By determining the concentrations of the lipoprotein classes in blood, one can therefore detect the presence of these disorders. The Frederickson classification system is summarized in Table I.

TABLE I

The Major Abnormal Lipoprotein Patterns[a]

| Type | Chylomicrons | LDL | VLDL | Floating beta Lipoproteins |
|------|--------------|-----|------|----------------------------|
| I    | +            |     |      |                            |
| IIa  |              | +   |      |                            |
| IIb  |              | +   | +    |                            |
| III  |              |     |      | +                          |
| IV   |              |     | +    |                            |
| V    | +            |     | +    |                            |

[a] "+" indicates elevated concentration.

In the past, measurement of total cholesterol and total triglyceride has been used to detect certain of these disorders. But because the various classes of lipoproteins contain cholesterol and triglyceride in different proportions as discussed above, determination of only total cholesterol and total triglyceride is not sufficient to differentiate among the six major abnormal lipoprotein patterns discussed above. It is therefore, necessary to determine the concentrations of lipoproteins rather than just lipids in order unequivocally to determine the types of abnormal lipoprotein patterns described by Frederickson, et al., and thus the associated disorders.

Furthermore, determination of lipoprotein concentrations allows more convenient calculation of lipid concentrations than with prior art methods. Prior art methods for determination of cholesterol and triglyceride concentrations require the subject to fast from ten to fourteen hours prior to withdrawal of the sample. This is a disadvantage, as discussed below. Further, prior art methods generally require extraction of the serum with various solvents to enhance their specificity. This requirement imposes an additional step on prior art lipid determination methods and is seen to be a further disadvantage. Moreover, no rapid screening technique for accurately determining the sum of cholesterol and triglyceride concentrations is known.

Three techniques have generally been used in the prior art to determine the concentrations of the various lipoprotein classes: visual evaluation of the plasma, electrophoresis, and ultracentrifugation. All three techniques generally require the subject to fast for ten to fourteen hours prior to the drawing of the sample to minimize the effect of exogenous chylomicrons on lipid measurements. It is a disadvantage of these techniques that they require this fasting, which is a hardship to the patient and makes him less willing to undergo these tests.

Visual evaluation of the plasma is not a quantative technique but is of use in detecting chylomicrons. When plasma stands in a tube at 0°-4° C. for 18-24 hours, the chylomicrons will rise to the top of the tube and are visible as a layer of "cream." Because of its lack of precision, this technique is unsatisfactory unless combined with another.

Electrophoresis is a relatively inexpensive and simple method compared to untracentrifugation but has several serious disadvantages. It is at best semiquantitative, and unequivocal interpretation often requires total serum cholesterol and triglyceride analysis. Therefore, the method is not independent and must be supplemented by other measurements. Also, quantification of the lipoprotein elctrophoresis bands is a difficult procedure, whether done by chemical determination of by densitometry.

While ultracentrifugation is a more easily quantified method for determination of the individual lipoprotein classes, it is both expensive and time-consuming. Because of the expense, it is not generally possible for blood analysis to be performed using this method by the physician himself or by one in his employ. In fact, this technique is generally not used clinically but only as a research tool, because of its difficulty and because of the expensive equipment required.

The difficulties attendant on the methods of electrophoresis and ultracentrifugation have led to the development of simpler trubidimetric methods.

For example, Stone, et al., Clin. Chim. Acta, 31 (1971) 333–354, have proposed measuring the turbidities of chylomicrons and VLDL in serum by nephelometry to obtain their concentrations. From these lipoprotein concentrations and a measurement of total serum cholesterol, the authors estimate the concentration of LDL. This method has the advantage of being rapid and simple, and does not require fasting by the subject. However, there are many sources of error, including minute scratches on the surface of the measuring cuvette and non-uniform standards.

Scholnick, et al., have also proposed a turbidimetric method for detection and identification of types of hyperlipoproteinema (Protides of the Biological Fluids of the 19th Coloquiuum 1971, H. Peeters, Ed., pp. 16 289-292). Scholnick, et al., teach a method based on the selective precipitation of lipoproteins by heparin in the presence of divalent cations. In this prior art method, three samples of serum from the blood of the patient under study are prepared and each is separately combined with a certain quantity of heparin (a sulfated polysaccharide), a divalent cation (Mg++ or Ca++), and (for certain samples) sodium ion. The procedure is described by Scholnick, et al., as follows:

"Two ml. of salt solution is added to each of three tubes. To tube one, 0.025 M Ca Cl$_2$, to tube two, 0.1 M MgCl$_2$ in 0.7% NaCl, and to tube three, 0.1 M MgCl$_2$ in 1% NaCl. To each of these is added 0.2 ml. of serum and the blank is read at 650 nm in a Coleman Jr. spectrophotometer. To tube one is added 0.01 ml. of 1% heparin in normal saline and to tubes two and three, 0.04 ml. of 5% heparin in normal saline. After the addition of heparin, the tubes are mixed and after 4 min. at room temperature, the turbidity is measured."

The trubidity in sample one is due to the insoluble complexes of chylomicrons, VLDL, and LDL; that in the second sample is due to the insoluble complexes of chylomicrons an VLDL; and that in the third sample is due to the insoluble complex of chylomicrons along. Scholnick, et al., have correlated these turbidities with the abnormal lipoprotein patterns of Frederickson, et al., in an attempt to provide a method for detecting types of hyperlipoproteinemia.

While the method of Scholnick, et al., is to be preferred over the three older techniques previously discussed, it also has certain disadvantages. First, sulfated polysaccharides in general and heparin in particular are expensive and scarce materials. The fact that more than 0.08 ml. of 5% heparin is needed to analyze one blood sample by this prior art method is seen to be a disadvantage. Second, three separate samples of serum are required for each analysis; this increases the manipulations required to preprare for the analysis and also increases the amount of blood which must be obtained to perform the analysis. Third, Scholnick, et al., teach no method for relating the trubidity measurements obtained by their technique to the concentrations of the various individual lipoprotein classes or to the sum of cholesterol and triglyceride concentration in the blood sample. That is, although a linear regression based on data from their laboratory shows a correlation between turbidity measurements obtained through their technique and independently-measured cholesterol or triglyceride concentrations, no method for accurately determining the concentration of individual lipoprotein classes is taught. There is also no teaching of a method for accurately determining the sum of cholesterol and triglyceride concentrations by a single measurement. This latter determination is of great value in screening patients for elevated levels of either material. Further, Scholnick, et al., teach no standardization techinque so that a single set of turbidities measured on a given spectrophotometer can be used to determine lipoprotein concentrations.

It is, therefore, an object of the present invention to provide a turbidimetric method for determining concentrations of individual liproprotein classes in blood. It is a further object to provide such a method which uses minimum of sulfated polysaccharide. It is a further object to provide such a method which uses a minimum of blood serum. It is a further object to provide such a method which involves only a single serum sample and thus a minimum of manipulation and equipment. It is a further object to provide such a method which does not require fasting by the subject prior to withdrawal of the blood sample. It is a further object to provide such a method whereby the sum of the cholesterol and triglyceride concentrations may be determined by a single measurement, thus permitting rapid screening for individuals with excessive levels of either material. It is also an object of the present invention to provide a turbidimetric method for determination of individual lipid concentrations in blood. It is still a further object to provide a standardization technique for relating the turbidimetric measurements obtained on a given spectrophotometer to the concentrations of the various lipoprotein classes or lipids.

SUMMARY OF THE INVENTION

It has now been discovered that a single-sample method for determining concentrations of individual lipoprotein classes in blood by turbidimetric measurements satisfies these objects. The present invention provides such a methods, including a technique for correlation between the turbidimetric measurements obtained and the concentrations of the individual lipoprotein classes and lipids. In the method of the invention, the blood serum is mixed with an effective concentration of an ionic-strength-sensitive agent for forming an insoluble complex with substantially all lipoproteins of classes present (excluding high density lipoproteins), and the ionic strength of the mixture (a function of the total concentration of ions present and of their valences) is raised in a step-wise fashion by addition of a salt solution to cause progressive dissolution of the complex of each lipoprotein class from highest to lowest density. Measurement of the trubidity of the resulting aqueous suspension of insoluble lipoprotein complex at each step and subtraction of each turbidity measurement (except the first) from the one before it yields the turbidities caused by the complexes of the individual lipoprotein classes. Using the correlation technique of the invention, the concentration of each lipoprotein class may then be calculated from the turbidity of its corresonding insoluble complex. Alternatively, the total concentration of complexed lipoprotein may be calculated at each step, and the individual concentrations (except the first) from the one before it. Further, the concentrations of lipids (cholesterol, triglyceride and their sum) may also be calculated from the lipoprotein complex turbidities.

There are generally three steps in this method, the lipoprotein forming insoluble complexes being indicated in parentheses: 1) initial (chylomicrons, VLDL, and LDL); 2) first increase in ionic strength (chylomicrons and VLDL); 3) second increase in ionic strength (chylomicrons only). Subtracting the turbidity in step 3 from that in step 2 yields the turbidity due to the complex of VLDL alone; subtracting the turbidity in step 2 from that in step 1 yields the turbidity due to the complex of LDL alone. The initial turbidity is a measure of the sum of cholesterol and triglyceride concentration, that in step 2 is a measure of triglyceride concentration, and the difference between these is a measure of cholesterol concentration.

The preferred ionic-strength-sensitive complexing agent of the invention is an aqueous solution of: 1) a sulfated polysaccharide such as, for example, heparin, dextran sulfate, and the like, and 2) the salt of a divalent cation such as, for example, magnesium ion, calcium ion, manganese ion, cobalt ion, and the like. The relative concentrations and identities of the two components of the complexing agent must be chosen so that substantially all lipoproteins of the classes present in the serum (except HDL) will be complexed at one ionic strength and only the lowest density class present in the serum will be complexed at some higher ionic strength. The preferred complexing agent is an aqueous solution of heparin and magnesium ion, the latter preferably obtained as magnesium chloride. The heparin should have a specific activity between about 140 and about 170 IU/mg and may be obtained from sheep lung, hog intestinal mucosa, and the like, as is known in the art. The preferred heparin is sodium heparin USP sold by Cohelfred Laboratories, Inc., Chicago, Illinois, which has an activity of about 157 USP units drug basis/mg.

While heparin is the preferred sulfated polysaccharide, dextran sulfate substituted for heparin in the preferred embodiment discussed below yields results which correlate well with those obtained using heparin.

While $Mg++$ is the preferred divalent cation, $Ca++$ (calcium chloride) or $Mn++$ (magnesium chloride) substituted for magnesium chloride in the preferred embodiment discussed below yields results which correlate well with those obtained using magnesium chloride. The divalent cation is preferably used as the chloride salt, but other monovalent anions, such as bromide and the like, may be used.

The concentration of the heparin in the preferred complexing agent should generally be between about 0.005% and about 0.05% by weight, preferably about 0.03% by weight of the weight of the solution. While there is some dependence of turbidity upon this concentration, especially for the second step of the method of the invention, this dependence can be accounted for by an appropriate choice of standard as discussed below.

The concentration of magnesium ion (magnesiun chloride) in the preferred complexing agent may be from about 0.025M to about 0.075M, preferably about 0.05M. Turbidity generally increases with increasing concentration of magnesium ion in the second and third steps of the method of the invention; this increase, however, may be compensated for by an adjustment in the standard as described below.

The ionic strength of the mixture may be raised by addition of a salt of monovalent cation such as, for example, sodium ion, potassium ion, and the like. The preferred material for raising the ionic strength of the mixture is sodium ion, preferably obtained as sodium chloride, but other monovalent salts, such as the bromide and the like, may be used. As the ionic strength (ionic concentration) of the solution is increased, the solubility of the various lipoprotein complexes also increases. Thus the complexes dissolve in a stepwise fashion beginning with the complex of the highest density lipoprotein as the ionic strength is increased to the appropriate levels as discussed below.

The pH of the solution must be chosen so that the complexing agent will be ionic-strength sensitive. Because it is known that sulfated polysaccharides alone (in the absence of divalent cations) will form insoluble complexes with lipoproteins at a pH more acid than that of blood serum, such a more acid pH is undesirable. Certin sulfated polysaccharides will even form complexes at neutral pH in the absence of divalent cations. These complexes are generally not ionic strength sensitive, however, The pH should, therefore, be generally greater than 7.25, preferably from about 7.25 to about 8.25 and more preferably about 7.50.

The concentration of monovalent cation (e.g., sodium chloride) in the second and third steps must be such as to cause the desired insoluble complex(es) to remain while another dissolves. Thus, for causing the dissolution of the complex of LDL in the second step, it has been discovered that the concentration of sodium chloride in the resulting solution should be between about 0.55% and about 0.80% by weight. For causing the dissolution of the VLDL complex in the third step, the concentration of sodium chloride in the resulting solution should be between about 0;.95% and about 1.15% by weight. Using the preferred heparin discussed above, the preferred range of sodium chloride in the solution in the second step is from about 0.60% to about 0.65% by weight. Likewise, the preferred concentration in the solution in the third step is from about 1.0% to about 1.1% using the preferred heparin.

The method of the invention should be practices at a relatively constant temperature, preferably between about 20° and about 30° C. The first step is somewhat sensitive to temperature changes (turbidity increasing with temperature), while the other two steps are relatively temperature-insensitive. The temperature sensitivity of the first step may be compensated for by correlation of the standard, as discussed below.

In a preferred embodiment of the method of the invention, a reagent solution is prepared comprising the ionic-strength-sensitive complexing agent (preferably heparin/$Mg++$), a buffer (if desired), and a bacteriostatic agent (if desired). This solution is then added to the blood serum with mixing and the method proceeds as outlined above. It is preferred for the methid of the invention that the reagent solution be added to the serum and not the reverse, because otherwise the turbidity produced varies depending on the length of time between addition and mixing and on the intensity of the mixing. Turbidities of 60% -100%higher are produced by addition of serum to reagent solution than vice-versa. When the solution is added to the serum, however, the turbidity produced is essentially independent of the length of time between addition and mixing and also of the intensity of the mixing. It is therefore, preferred for accuracy and precision that the solution be added to the serum rather than vice-versa.

Because the method of the invention involves only one sample of blood serum and one addition of heparin it obviates those disadvantages of the method of Scholnick, et al., discussed above. The method of the invention also does not require a blank measurement to be made. Further, the method of the invention is a single-sample one and consequently involves manipulation of only a single sample as opposed to three samples in the method of scholnick, et al.; the method of the invention is, therefore, simpler and easier to perform. Still further, the method of the invention allows calculation of the concentrations of the individual lipoprotein classes, as not provided by the Scholnick method. The method of the invention also provides a simple method for measurement of lipid concentrations in blood and more particularly for rapid determination of the sum of cholesterol and triglyceride concentration in a single measurement step. Finally, the method of the invention includes a standard (discussed below), whereby anyone desirous of using it may calculate the concentration of the individual lipoprotein classes or lipids from a single set of turbidimetric measurements on a given spectrophotometer.

The following preferred embodiment is provided to illustrate the method of the invention. All percentages are by weight.

DESCRIPTION OF THE PREFERRED EMBODIMENT

An aqueous solution having the following composition is prepared:
0.02% heparin
0.05 M magnesium chloride
0.005 M imidazole (buffer)
0.01% thimerosal (bacteriostatic agent)
pH 7.50

To 0.1 ml. of fresh serum is added 2 ml. of the above solution with mixing. The whole is allowed to stand at room temperature for approximately 30 minutes and the turbidity is then measured at 650 nm. This turbidity is measured in absorbance (OD) units and is due to the insoluble complexes of chylomicrons, VLDL, and LDL.

To the above turbid solution is then added 0.1 ml. of a 12.60% aqueous solution of sodium chloride containing 0.01% thimerosal; this addition causes the sodium chloride concentration of the resulting solution to be 0.60%. The whole is mixed and allowed to stand for a further 15 minutes and the turbidity is again measured. This turbidity is due to the insoluble complexes of chylomicrons and VLDL.

To this solution is then added 0.1 ml. of a 9.40% aqueous solution of sodium chloride containing 0.01% thimerosal; this addition causes the sodium chloride concentration in the resulting solution to be 1.0%. The whole is mixed and allowed to stand for 15 minutes and the gtrubidity is measured. This turbidity is due only to the insoluble complex of chylomicrons.

The third turbidity measurement is subtracted from the second and the second is subtracted from the first to give the individual turbidity measurements; from these individual turbidity measurements the concentrations of each individual lipoprotein class and of each lipid class may be calculated as explained below.

It should be understood that one may vary the technique of this preferred embodiment considerably while remaining within the scope of the present invention.

Thus, the time of incubation may be considerably shortened if desired. If the method is to be practiced manually then 15–30 minutes is a reasonable time period. If, however, the method is to be prracticed as an automated procedure on a machine, then the incubation period could be shortened to a little as one minute. It should be understood that the turbidity produced is dependent on the time between mixing and measurement; that is, after the addition of the complexing agent to the serum sample with mixing in the first step of the method, the turbidity increases sharply and then levels off. Approximately 95% of the turbidity is developed within 30 minutes after mixing; therefore, any time error in making a measurement after 30 minutes of incubation has a negligible effect, making this incubation time preferably for the first step of a manual operation.

In the second and third steps the decrease in turbidity is essentially complete within 15 minutes after mixing; this time could be decreased to about 5 minutes for each step if automated procedures were being employed. The difference between turbidities produced after a 5 minute incubation may be compensated for by an adjustment in the standard, as discussed below.

By correlation of turbidity data from the method of the invention with independently-obtained lipoprotein and lipid concentrations for a range of subjects, correlation diagrams exemplified in the FIGS. may be prepared. By means of such diagrams, the concentration of lipoprotein and lipid classes may be obtained from the turbidity due to the corresponding complexes.

The method of the present invention exhibits several advantages over the method of prior art. The preferred embodiment of the present invention requires only 1/11 as much heparin and 1/6 as much blood serum as the method of Scholnick, et al., discussed above. The present method allows calculations of the concentration of the individual lipoprotein classes. Further, the present method is simpler than those of the prior art because it is a single-sample method and lends itself readily to automation.

While it is contemplated in the method of the invention that the concentration of the classes of lipoproteins in a blood sample may be obtained by the correlation-diagram technique described above, a more preferred embodiment of the invention provides a standardizing method as described below. Because the correlation diagram technique described above is sensitive to the particular spectrophotometer used, one would have to make a new correlation diagram for each individual spectrophotometer. The standardizing method of the invention, however, allows one to use any turbidity measuring means or spectrophotometer of the designated type without preparing a new correlation diagram.

In order that one making measurements using the method of the invention may be able accurately to compute the concentrations of the individual lipoprotein classes without preparing corelation diagrams, a standardizing method is provided. Prior to the present invention, there had been no such standard. One cannot conveniently use a primary test for standardization of lipoprotein measurements because lipoprotein samples are not stable over time. It is, therefore, necessary to utilize a secondary standar-that is, a stable material other than lipoprotein complex which has turbidometric properties similar to those of a particular insoluble lipoprotein complex. The search for a secondary standard is complicated by the fact that not all turbidity measuring means give the same optical density reading for two samples having the same turbidity. This phenomenon arises because different samples having the same turbidity often scatter light differently and so give different absorbance values. Further, different spectrophotometers accept different amounts of scattered light, which also affects the absorbance value. The criterion for selecting a secondary standard, therefore, is that it have light absorbance characteristics corresponding to those of the insoluble lipoprotein complex(es) for which it is to be a standard. This criterion means that the standard of the invention must mimic the insoluble complex for which it is to be a standard in numerous turbidity measuring devices, allowing standardization of these devices.

It has now been discovered that certain aqueous suspensions of latex particles provide such secondary standards for the turbidimetric measurements of the method of the invention. Particles of polystyrenedivinylbenzene, polystyrene, and the like are exemplary of thos useful in the present standardization method. The particle sizes should be generally in the order of about 6 microns, although particles as small as about 0.2 microns and as large as about 25 microns may be used. Standard suspensions may be prepared by mixing particles of one or more different types with water and comparing the light absorbance characteristics of the resulting suspensions with those of the insoluble lipoprotein complex(es) for which they are to be standards. The composition of the suspensions are changed until the light absorbance characteristics of the suspension correspond to those of the lipoprotein complex(es) One way in which the light absorbance chracteristics of the suspensions may be compared with those of the insoluble complex for which they are to be standards is to measure the light scattering pattern of each of these materials through 360°. That is, by measuring the proportion of light scattered by a standard suspension and an insoluble lipoprotein complex at all angles from the incident light beam and comparing the resulting patterns, one can determine whether the standard suspension mimics the complex. If the patterns are substantially identical, then the suspension is a good secondary standard for that insoluble complex. While the light scattering pattern produced by a suspension is somewhat dependent on the particle concentration, the absorbance of the suspension is essentially linearly related to its concentration.

Latex suspensions have previously been used for the calibration of light scattering instruments. However, the only criteria for such suspensions were that they be reproduceable and exhibit some scattering. The precise size of the particles was not considered important, very small particles generally being used. The suspensions of the present invention, on the other hand, must mimic the light scattering properties of each lipoprotein complex for a particular type of spectrophotometer. Hence, the size of the particles used is critical.

Because these suspensions are secondary standards, they must be correlated to the actual lipoprotein turbidities before they are useable. This procedure will be described for only one standard since the others are correlated in an identical manner. First, one performs a number of repetitions of the method of the invention and obtains a standard curve relating turbidity (absorbance) of a complex of one lipoprotein class to the chemically-determined concentration of that particular class of lipoproteins (similar to the Figures). One then prepares several different dilutions of a suspension which is a standard of the particular lipoprotein class, these dilutions having widely varying abosrbances which include the absorbances reported for the particular class of lipoprotein complex. Each concentration of the standard suspension is then labeled with the concentration of the particular lipoprotein class associated with the absorbance measured for it, thereby providing an effective secondary standard. It should be understood that the standard can be correlated with a lipoprotein complex turbidity obtained under any desired set of conditions; e.g., temperature, incubation time, concentration of reagents, etc. Alternatively, a particular standard suspension could be associated with one of several lipoprotein concentrations depending on the temperature, pH, incubation time, etc. The correlation of the standard is illustrated below.

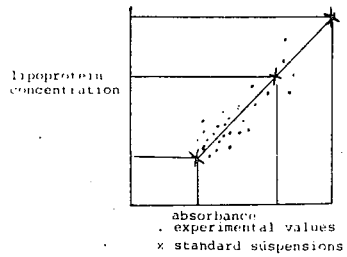

This standard curve will be strictly valid only for the type of spectophotometer (e.g., Coleman, Jr.) on which the measurements were made. It should be understood, however, that such a relationship between the standard and lipoprotein concentration could be made for any type of turbidity measuring means and is not limited to any particular instrument disclosed herein.

One preferred group of secondary standards for use in the method of the present invention comprises aqueous suspensions of laytex particles ranging in size from about 0.20 to about 6 microns and more preferably suspensions of the following:

| Suspension type | Weight percent by solids |
|---|---|
| A | 96% 5.7 micron polystyrene divinylbenzene |
|   | 4% 0.234 micron polystyrene |
| B | 100% 1.01 micron polystyrene |
| C | 75% 1.01 micron polystyrene |
|   | 25% 0.80 micron polystyrene |

Type A is a standard for the mixture of complexes resulting from the first step of the method of the invention, type B for the mixture resulting from the second step, and type C for the complex resulting from the third step. Each of these suspension types may be diluted to appropriate absorbance values to yield a plurality of standards for each complex or mixture of complexes. Preferred absorbance values for type A are 0.30 and 0.15; for type B are 0.15 and 0.05; and for type C are 0.15 and 0.05.

One preferred secondary standard for use in determination of lipid concentratioons (cholesterol, triglyceride, and their sum) is an aqueous suspension of 5.7 micron polystyrene/divinylbenzene. Dilutions of this aqueous suspension yield good secondary standards for all three determinations. Standards for cholesterol preferably have absorbance of about 0.30 and 0.15, standards for triglyceride preferably have absorbances of about 0.15 and 0.05, and standards for the sum of cholesterol and triglyceride perferably have absorbances of about 0.30 an 0.15.

To convert turbidimetric data obtained by the method of the invention into the concentrations of the lipoprotein classes, one reverses the above procedure. Using the various concentrations of the standard suspension for each step of the method, one measures the absorbance of each standard in the spectrophotometer to be used and plots its absorbance against the lipoprotein concentration associated with it. A straight line between these points yields a standard curve for the particular step and spectrophotometer which allows the measured turbidities to be converted into lipoprotein concentrations.

In a similar fashion, one may determine lipid concentrations by relating chemically-determined lipid concentrations to the turbidities of the complexes of the lipoprotein classes containing these lipids. Thus, the initial turbidity (LDL, VLDL, and Chylomicrons) is correlated with the sum of cholesterol and triglyceride concentrations, the second turbidity (VLDL and chylomicrons) is corrrelated with triglyceride concentration, and the difference between the initial and second turbidities (LDL) is correlated with cholesterol concentration.

The method of the invention is illustrated by the following examples.

EXAMPLE I

An examination of 60 serum samples for serum cholesterol and triglyceride was conducted using the test method of the invention. Cholesterol values ranged from 135 to 376 mg/ml and triglyceride values from 37 to 846 mg/100 ml. Reagents were prepared as follows:

Solution A:
 0.02% heparin (Fisher Scientific Co.)
 0.05 M magnesium chloride
 0.005 M imidazole
 0.01% thimerosal
 pH 7.5

Solution B:
 28.7% sodium chloride
 0.01% thimerasol

To 0.1 ml. of each serum sample was added 4 ml. of Solution A with mixing. The whole was allowed to stand at room temperature for 30 minutes, after which time the turbidity (due to LDL, VLDL, and chylomicrons) was measured at 650 nm. This turbidity was called "turbidity I."

To this solution was then added 0.1 ml. of Solution B with mixing. The whole was allowed to stand at room temperature for 15 minutes, after which time the turbidity (due to VLDL and chylomicrons) was measured at 650 nm. This turbidity was called "turbidity II."

The correlation of turbidity I with the sum of cholesterol and triglyceride concentrations is shown in FIG. 1; that between turbidity II and triglyceride concentration in FIG. 2; and that between tubidity I minus turbidity II and cholesterol concentration in FIG. 3. The standard deviation (S.D.) for each correlation shown in each figure demonstrates the utility of this method for determination of serum lipid concentrations.

EXAMPLE II

The procedure of Example I above was repeated for 144 rendomly-selected blood serum samples, using the preferred reagents and concentrations disclosed above. The reagents were:

Solution A:
 0.02% heparing (Cohelfred)
 0.05 M mangesium chloride
 0.005 M imidazole
 0.01% thimerosal
 pH 7.5

Solution B:
 12.60% sodium chloride
 0.01 thimerasol

The procedure of Example I was followed except that 2 ml of Solution A was used instead of 4 ml.

The following standard deviations and correlation coefficients were obtained:
a. turbidity I correlated with the sum of cholesterol and triglyceride concentrations: 25 mg/100 ml, 0.94;
b. tirbidity Ii correlated with triglyceride concentration: 28 mg/100 ml, 0.86;
c. turbidity I minus turbidity II correlated with cholesterol concentration: 21mg/100 ml, 0.80.

These standard deviations and correlation coefficients further demonstrate the utility of the present invention.

EXAMPLE III

Following the procedure of Example II, 72 randomly-selected blood samples were tested for lipoprotein concentration. The additional reagent solution C (comprising aqueous 9.4% sodium chloride and 0.01% thimerosal) was used, 0.1 ml. of which was added with mixing after the masurement of "turbidity II." The whole was then allowed to stand at room temperature for 15 minutes, after which time the turbidity (due to chylomicrons) was measured at 650 nm. This turbidity was called "turbidity III." The final sodium chloride concentration in the solution was 1.0% by weight.

The following standard deviations and correlation coefficients were obtained:

| Turbidity | Lipoprotein(s) | Standard Deviation (mg/100ml) | Correlation Coefficient |
|---|---|---|---|
| I-II | LDL | 20.9 | 0.83 |
| II-III | VLDL | 15.7 | 0.86 |
| II | VLDL & CHYLO | 1.0 | 0.89 |
| III | CHYLO | 6.6 | 0.76 |

These results illustrate the utility of the present method for determining the concentrations of the individual lipoprotein classes.

The above Examples have been given only for purposes of illustrating the method of the present invention, the scope of which is defined by the following claims.

What is claimed is:

1. A single-sample method for determining the concentrations of low density lipoprotein (LDL), very low density lipoprotein (VLDL) and chylomicrons (CHYLO) in blood which comprises:
   a. mixing the serum of said blood with an ionic-strength-sensitive agent for forming an insoluble complex with substantially all of said LDL, said VLDL, and said CHYLO, comprising a sulfated polysaccharide and the salt of a divalent cation whereby turbidity is produced in said mixture;
   b. measuring the tubidity of said mixture;
   c. increasing the ionic strength of the mixture formed in step a) to a value whereby the LDL complex dissolves, so that the remaining turbidity of said mixture is due primarily to the insoluble complexes of VLDL snd CHYLO;
   d. measuring said remaining turbidity of said mixture;
   e. increasing the ionic strength of the mixture formed in step c) to a value whereby VLDL complex dissolves, so that the final turbidity of said mixture is due primarily to the insoluble complex of CHYLO;
   f. measuring said final turbidity of said mixture;
   g. and utilizing said turbidities to determine the concentration of LDL, VLDL, and chylomicrons.

2. The method according to claim 1 wherein the turbidities are utilized to determine the concentration of LDL, VLDL and chylomicrons by
   i. subtracting the turbidity obtained in step d) from that obtained in step b) to obtain the turbidity due to the insoluble complex of LDL alone and determining the concentration of said LDL therefrom;
   ii. subtracting the turbidity obtained in step f) from that obtained in step d) to obtain the turbidity due to the insoluble complex of VLDL alone and determining the concentration of said VLDL therefrom;

iii. determing the concentration of said chylomicrons from the turbidity obtained in step f.

3. The method according to claim 1 wherein the turbidities are utilized to determined the concentration of LDL, VLDL and chylomicrons by
   i. determining the concentration of total LDL, VLDL and CHYLO from the turbidity obtained in step b);
   ii. determining the concentration of total VLDL and CHYLO from the obtained in step d);
   iii. determining the concentration of chylomicrons from the turbidity obtained in step f);
   iv. subtracting the concentration of total VLDL and CHYLO obtained in step d) from the concentration of total LDL, VLDL, and CHYLO obtained in step b) to get the concentration of LDL; and
   v. subtracting the concentration of CHYLO obtained in step f) from the concentration of CHYLO obtained in step f) from the concentration of total VLDL and CHYLO obtained in step d) to get the concentration of VLDL.

4. The method of claim 1 wherein the concentration of said LDL, said VLDL, and said CHYLO lipoproteins is determined by:
   a. measuring for each of said lipoproteins to be determined, the turbidy of a plurality of aqueous suspensioms of latex particles ranging in size from 0.2 microns to about 25 microns, said suspensions having different absorbances, each of said absorbances corresponding to the turbidity of an aqueous suspension of an insoluble complex of said lipoprotein having a known concentration of said lipoprotein;
   b. establishing a standard curve of turbidity against lipoprotein concentration for each of said lipoproteins to be determined, from the measured turbidity from step a) of each of said suspensions and the known lipoprotein concentrations corresponding to each of said suspensions; and
   c. utilizing said standard curve to determine the concentration of each lipoprotein to be determined from the turbidity of an insoluble complex thereof.

5. The method of claim 4 wherein the latex particles have a sizes from about 0.20 microns to about 6 microns.

6. The method of claim 1, wherein said ionic-strength-sensitive complex agent is the combination of heparin and a magnesium salt; wherein said LDL complex is caused to dissolve by addition of sufficient sodium chloride to make its concentration in the range from about 0.55% to about 0.80% by weight in the mixture; and wherein said VLDL complex is caused to dissolve by addition of sufficient sodium chloride to make the concentration of said sodium chloride be in the range from about 0.95% to about 1.15% by weight in the mixture.

7. The method of claim 6, wherein the concentration of heparin in the mixture is in the range from about 0.005% to about 0.05% by weight, the magnesium salt is present in the range from about 0.025 to about 0.75 molar concentration, and the pH is in the range from about 7.25 to about 8.25.

8. The method of claim 6, wherein the heparin and magnesium salt are combined and then added to the serum in step a).

9. A single-sample method for determining the concentrations of triglyceride and cholesterol in blood by forming insoluble complexes of low density lipoprotein (LDL), very low density lipoprotein (VLDL) and chylomicrons (CHYLO) which comprises:
   a. mixing the serum of said blood with an ionic-strength-sensitive agent for forming an insoluble complex with substantially all of said LDL, said VLDL, and said CHYLO comprising an aqueous solution of a sulfated polysaccharide and the salt of a divalent cation, whereby turbidity is produced in said mixture;
   b. measuring the turbidity of said mixture and determining the sum of the concentrations of triglyceride and cholesterol therefrom;
   c. increasing the ionic strength of the mixture formed in step a) to a value whereby the LDL complex dissolves, so that the remaining turbidity of said mixture is due primarily to the insoluble complexes of VLDL and CHYLO;
   d. measuring said remaining turbidity of said mixture and determining the concentration of triglyceride therefrom;
   e. subtracting the concentration of triglyceride obtained in step d from the sum of the concentrations of triglyceride and cholesterol obtained in step b to get the concentration of cholesterol.

10. A single-sample method for determining the concentrations of triglyceride and cholesterol in blood by forming insoluble complexes of low density lipoprotein (LDL), very low lipoprotein (VLDL) and chylomicrons (CHYLO) which comprises;
    a. mixing the serum of said blood with an ionic-strength-sensitive agent for forming an insoluble complex with substantially all of said LDL, said VLDL, and said CHYLO comprising an aqueous solution of a sulfated polysaccharide and the salt of a divalent cation, whereby turbidity is produced in said mixture;
    b. measuring the turbidity of said mixture;
    c. increasing the ionic strength of the mixture formed in step a) to a value whereby the LDL complex dissolves, so that the remaining turbidy of said mixture is due primarily to the insoluble complexes of VLDL and CHYLO;
    d. measuring said remaining turbidity of said mixture and determining the concentration of triglyceride therefrom;
    e. subtracting the turbidity obtained in step d) from that obtained in step b) to obtain the turbidity due to the insoluble complex of LDL alone and determining the concentration of cholesterol therefrom.

11. The method of claim 10 wherein the concentration of said triglyceride and cholesterol lipids is determined by:
    a. measuring for each of said lipids to be determined, the turbidity of a plurality of aqueous suspensions of latex particles ranging in size from about 0.2 microns to about 25 microns, said suspensions having different absorbances, each of said absorbances corresponding to the turbidity of an aqueous suspension of an insoluble complex containing said lipid in a known concentration;
    b. establishing a standard curve of turbidity against lipid concentration for each of said lipids to be determined, from the measured turbidity from step a) of each of said suspensions and the known lipid concentration corresponding to each of said suspensions; and
    c. utilizing said standard curve to determine the concentration of each lipid to be determined from the tubidity of an aqueous suspension of an insoluble complex of lipoprotein containing said lipid 12. The method of claim 11 wherein the latex particles are polystyrenedivinylbenzene having a size of about 6 microns.

13. The method of claim 12 wherein there are two of said suspensions for each lipid to be determined and said different abosorbances are about 0.15 and about 0.05 for triglyceride, and about 0.30 and about 0.15 for cholesterol.

14. The method of claim 10 wherein said ionic-strength-sensitive complex agent is the combination of heparin and a magnesium salt and wherein said LDL complex is caused to dissolve by addition of sufficient sodium chloride to make the concentration of said sodium chloride be in the range from about 0.55% to about 0.80% by weight in the mixture.

15. The method of claim 14 wherein the concentration of heparin in the mixture is in the range from about 0.005% to about 0.05% bt weight, the magnesium salt is present in the range from about 0.025 to about 0.075 molar concentration, and the pH is the range from about 7.25 to about 8.25.

16. The method of claim 14 wherein the heparin and magnesium salt are combined and then added to the serum in step a).

17. A single-measurement method for rapidly determining the sum of the concentrations of triglyceride and cholesterol in blood by forming insoluble complexes of low density lipoprotein (LDL), very low density lipoprotein (VLDL) and chylomicrons (CHYLO) which comprises:
   a. mixing the serum of said blood with an ionics-strength sensitive agent for forming an insoluble complex with substantially all of said LDL, said VLDL, and said CHYLO comprising an aqueous solution of a sulfated polysaacharide and the salt of a divalent cation, whereby turbidity is produced in said mixture; and
   b. measuring the turbidity of said mixture and determining the sum of the concentrations of triglyceride and cholesterol therefrom.

18. The method of claim 17 wherein the sum of the concentration of trigylceride and cholesterol in blood is determined by:
   a. measuring the turbidity of a plurality of aqueous suspensions of latex particles ranging in size from about 0.2 microns to about 25 microns, and suspensions having different absorbances, each of said absorbances corresponding to the turbidity of an aqueous suspension of insoluble complexes of said LDL, said VLDL, and said CHYLO, said complexes having a known sum of concentrations of triglyceride and cholesterol;
   b. establishing a standard curve of turbidity against concentrations, from the measured turbidity from step a) of each of said suspensions and the known sum of concentrations of triglyceride and cholesterol corresponding to each of said suspensions; and
   c. utilizing said standard curve to determine the sum of concentrations of triglyceride and cholesterol from the turbidity of an aqueous suspension of insoluble complexes of said LDL, said VLDL, and said CHYLO.

19. The method of claim 18 wherein the latex particles are polystyrenedvinylbenzene having a size of about 6 microns.

20. The method of claim 19 wherein there are two of said suspensions and said different absorbances are about 0.30 and about 0.15.

* * * * *